United States Patent [19]

Perlov et al.

[11] Patent Number: 4,498,850

[45] Date of Patent: Feb. 12, 1985

[54] METHOD AND DEVICE FOR FLUID TRANSFER

[76] Inventors: Gena Perlov, 18 Disraeli St., Haifa; Samuel Tuchman, 15 Hanarkissim St., Kiryat Bialik, both of Israel

[21] Appl. No.: 256,522

[22] Filed: Apr. 22, 1981

[30] Foreign Application Priority Data

Apr. 28, 1980 [IL] Israel .................................. 59942

[51] Int. Cl.³ .............................................. F04B 43/14
[52] U.S. Cl. .................................... 417/322; 417/413; 417/474
[58] Field of Search ............... 417/413, 474, 479, 412, 417/322, 475, 480, 395; 92/103 M; 310/25, 12, 36

[56] References Cited

U.S. PATENT DOCUMENTS

| | | | |
|---|---|---|---|
| 2,630,760 | 3/1953 | Ryba | 417/413 |
| 2,653,552 | 9/1953 | Geeraert | 417/395 X |
| 2,893,041 | 7/1959 | Schafer | 310/12 |
| 3,674,946 | 7/1972 | Winey | 310/25 |

FOREIGN PATENT DOCUMENTS

| | | | |
|---|---|---|---|
| 172516 | 9/1968 | Fed. Rep. of Germany | 417/412 |
| 1455664 | 11/1976 | United Kingdom | 417/395 |

*Primary Examiner*—Richard E. Gluck
*Assistant Examiner*—Peter M. Cuomo
*Attorney, Agent, or Firm*—Murray Schaffer

[57] ABSTRACT

There is provided a method and device for fluid transfer. The device comprises a housing-like body with a wall having a concavity. Inside the housing there is disposed a magnetically activatable diaphragm capable of forming, in conjunction with the concavity, one or more pocket-like chambers. The housing also includes an inlet and outlet aperture. The device includes a plurality of means for producing magnetic fields arranged in proximity to the concavity and adapted to generate, in a predeterminable sequence, a plurality of magnetic fields of controllably changing polarities and intensities producing cycles of dynamic deflections of the diaphragm. By means of the magnetically generated dynamic deflections of the diaphragm, the pocket-like chambers are peristaltically manipulated to move fluid from the region of the inlet aperture through which the fluid is drawn in, towards the region of the outlet aperture, through which the fluid is expelled.

15 Claims, 63 Drawing Figures

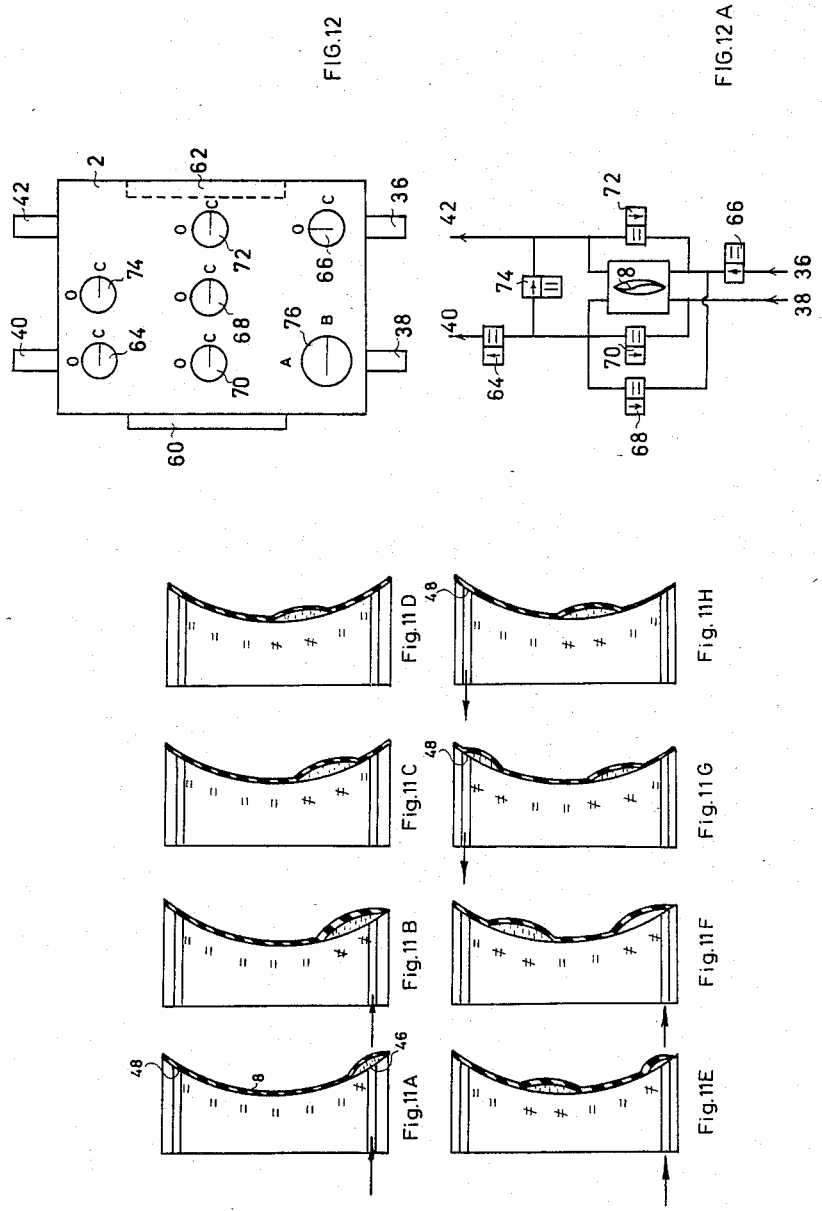

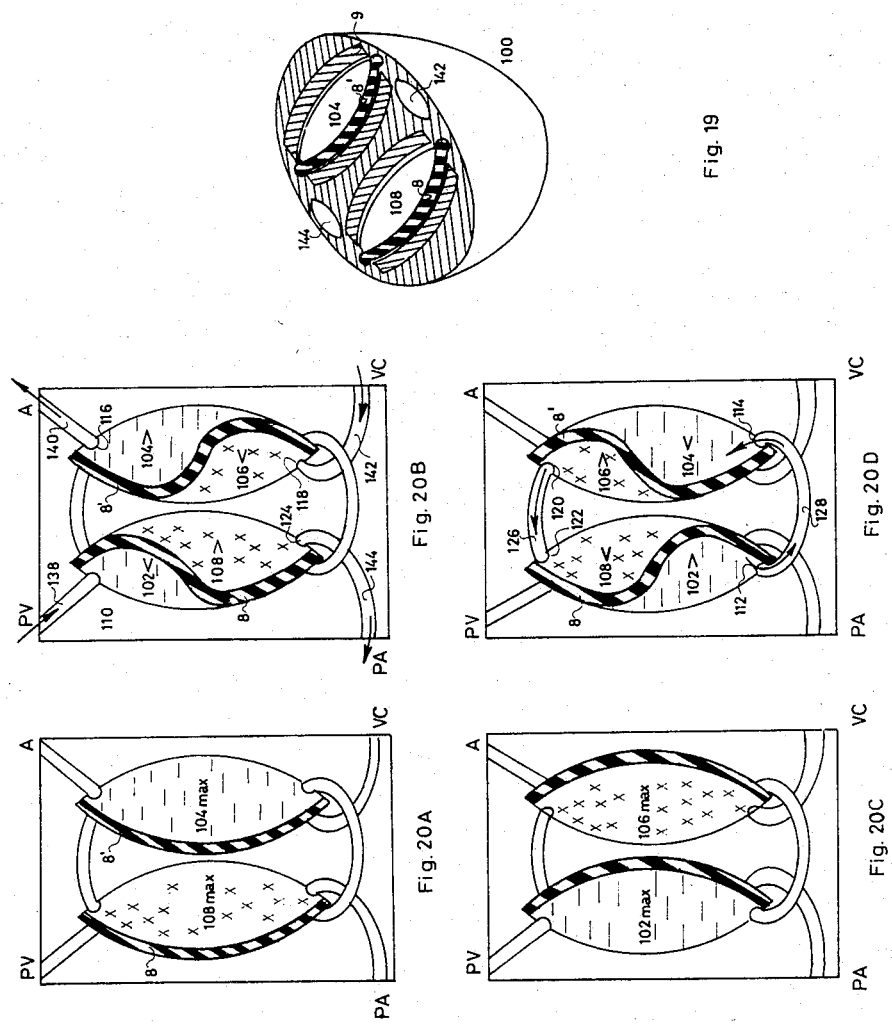

METHOD AND DEVICE FOR FLUID TRANSFER

The present invention relates to a device and to a method for fluid transfer.

The number of existing types of such devices, also known under the more specific terms of pumps, is very great, even if only positive-displacement pumps are considered, i.e., pumps that trap the fluid to be transferred in discrete portions, which are subsequently expelled from the pump. Most of these pumps are of the fixed-displacement type, that is, the volume of the above discrete fluid portions is given by the pump geometry and the output of these pumps can be changed only by changing the speed of their drives. As most of these devices use the relatively cheap constant-speed electric motors, their outputs are fixed, unless a different motor or some sort of speed-changing transmission is used. While variable gear transmissions or electronic speed control are known, these are relatively expensive devices. The same holds true also for variable-displacement pumps, which are quite complicated mechanically and are failure-prone unless carefully maintained. None of these prior-art pumps can be used for more than a very limited number of different applications, thus a gear pump cannot be used as vacuum pump or a screw pump as compressor. All of the prior-art-pumps are subject to wear both of their own moving parts (bearings, pistons, vanes, gears, etc.) and of their power sources (electric motors, gear transmissions, etc.). Another disadvantage of most prior-art pumps is that their drives have to be designed for the maximum rated pressure these pumps are to be used for and their use for lower-pressure applications is therefore wasteful of energy.

It is one of the objects of the present invention to overcome these and other difficulties and disadvantages, and to provide a fluid-transfer device which is largely universal in its applicability, is extremely compact, has only one moving part, is completely frictionless and, therefore, wear-proof and maintenance-free, has a steplessly variable output rate and can be adjusted to consume no more energy than required for a given pressure and output rate to be attained.

This the invention achieves by providing a device for fluid transfer comprising:
- a housing-like body with at least one wall having at least one concavity;
- at least one, at least partly magnetically activatable diaphragm capable of forming, in conjunction with said concavity, one or more pocket-like chambers;
- at least one inlet and one outlet aperture;
- a plurality of means for producing magnetic fields arranged in proximity to said concavity and adapted to generate, in a predeterminable sequence, a plurality of magnetic fields of controllably changing polarities and intensities producing cycles of dynamic deflections of said diaphragm, whereby, by means of said magnetically generated dynamic deflections of said diaphragm, said pocket-like chambers are peristaltically manipulated to move fluid from the region of said inlet aperture through which said fluid is drawn in, towards the region of said outlet aperture, through which said fluid is expelled.

The invention also provides a method for fluid transfer comprising:

(a) providing a housing-like body with at least one concavity, at least one, at least partly magnetically activatable diaphragm capable of forming, in conjunction with said concavity, one or more pocket-like chambers, at least one inlet and one outlet aperture, a plurality of means for producing magnetic fields arranged in proximity to said concavity, and control means for said field-producing means;

(b) generating with the aid of said field-producing means a plurality of magnetic fields and changing in a predeterminable sequence and with the aid of said control means the polarities and intensities of said magnetic fields in such a way as to produce cycles of dynamic deflections of said diaphragm, by means of which magnetically generated dynamic deflections said pocket-like chambers are peristaltically manipulated to move fluid from the region of said inlet aperture through which said fluid is drawn in, towards the region of said oulet aperture, through which said fluid is expelled.

In addition, the invention also provides an artificial, implantable heart, comprising:
- a housing-like body defining and delimiting at least one cavity;
- at least one, at least partly magnetically polarizable diaphragm capable of dividing said cavity into at least two pocket-like chambers;
- at least one inlet and one outlet aperture connectable to blood-delivering and blood-receiving blood vessels respectively;
- a plurality of electromagnets arranged in proximity to said cavity and adapted to generate, in a predeterminable sequence, a plurality of magnetic fields of controllably changing polarities and intensities, producing cycles of dynamic deflections of said diaphragm, which dynamic deflections cause the volume of at least one of said pocket-like chambers to be progressively diminished and, simultaneously, the volume of at least one other pocket-like chamber to be progressively increased, whereby blood is expelled from said diminishing-volume chamber into said blood-receiving blood vessels, while blood is drawn into said increasing-volume chamber from said blood-delivering blood vessels.

Further advantages of the fluid-transfer device according to the invention are as follows:

Pressure and output rate can be regulated either separately or simultaneously.

The device has no "dead" or "lost" volume.

None of the parts of the device requires precision machining, its manufacture therefore being relatively inexpensive.

The universality of the concept of the device facilitates its use for every type of fluid and all operational modes of such fluid-transfer devices as in-line pumps, peristaltic (or perfusion) pumps, metering pumps, artificial hearts, modular units with integral internal routing means permitting a plurality of such units to be joined to constitute: hydraulic pumps, vacuum pumps, compressors, mixer systems operating at precise ratios, etc.

While the invention will now be described in connection with certain preferred embodiments with reference to the following illustrative figures so that it may be more fully understood, it is stressed that the particulars shown and described are by way of example and for purposes of illustrative discussion only and are presented in the cause of providing what is believed to be the most useful and readily understood description of the principles and conceptual aspects of the invention.

In this regard no attempt is made to show structural details of the apparatus and its constituents in more detail than is necessary for a fundamental understanding of the invention, the description taken with the drawings making apparent to those skilled in the art how the several forms of the invention may be embodied in practice.

In the drawings:

FIGS. 11A to 11H are schematic reprsentations of the operational stages of the device of FIG. 10;

FIG. 12 shows a general view of a modular cell according to the invention;

FIG. 12A is a diagrammatic representation of the internal ducting of the modular cell of FIG. 12;

FIG. 19 is a perspective view, in cross section along a plane normal to the axis, of the artificial heart according to FIG. 18;

FIGS. 20A to 20D are schematic representations of different operational stages of the artificial heart according to FIG. 18;

Figure 1:
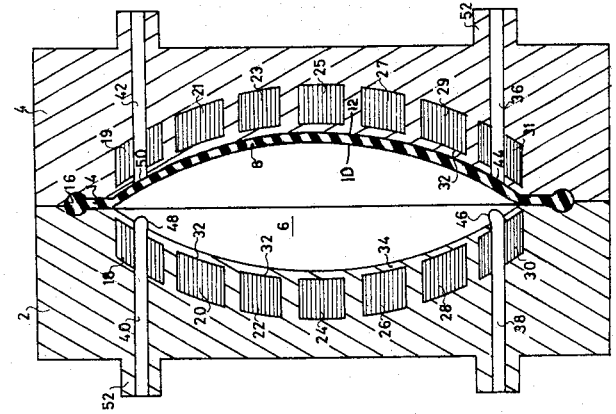
FIG. 1 is a schematic, cross-sectional view of a basic embodiment of the device according to the invention.
Figure 2:
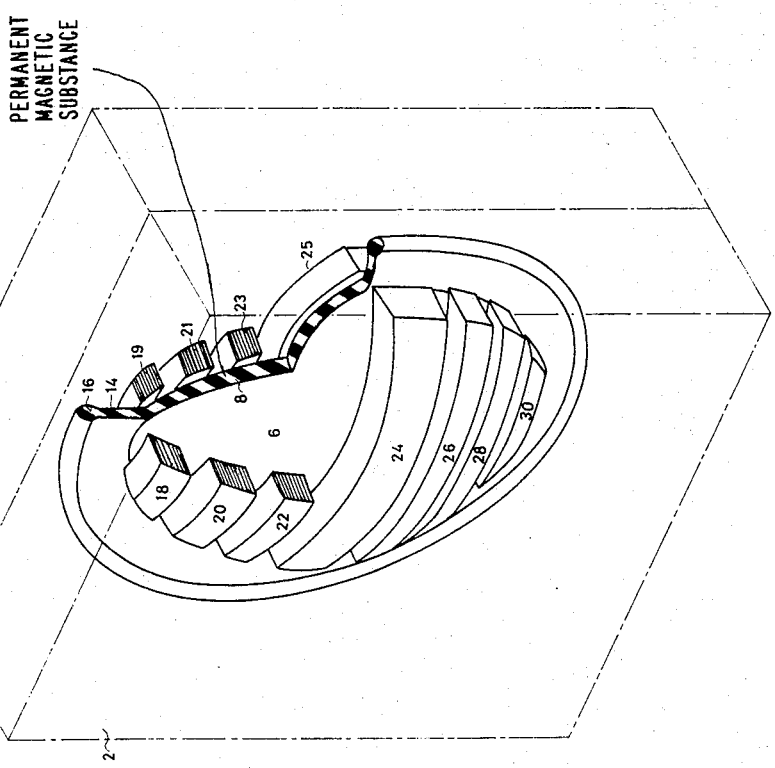
FIG. 2 is a perspective view, partly in cross section, of the interior of the embodiment of FIG. 1.

There is seen in FIGS. 1 and 2 a basic embodiment of the pump according to the invention, comprising a split housing-like body consisting of two halves 2 and 4 which, between them, define and delimit a lenticular cavity 6. Geometrically, this cavity 6 can be regarded as being produced by the interpenetration of two concave surfaces of revolution facing one another with their concavities. While in this particular embodiment these surfaces are spherical, they may be generated also by conic sections other than circles, or indeed, by any plane curve. In still other embodiments, the cavity 6 may be formed not by surfaces of revolution, but by twisted or spiraling surfaces. Yet another embodiment may have a toroidal cavity of either a concave-convex, plano-convex or biconvex cross section.

Together, the concavities in the two housing halves 2 and 4 constitute the cavity 6. The latter is dividable into separate, pocket-like chambers by a flexible diaphragm 8 having magnetic properties, that is, being capable of flexing and, due to the admixture to its basic plastic or elastomeric material of a ferromagnetic substance, being permanently magnetizable. Magnetization is carried out in such a way that the diaphragm is magnetically polarized in a direction perpendicular to its surfaces, that is, one of its surfaces, e.g., surface 10 is a permanent north pole, the other, e.g., surface 12, a permanent south pole.

The diaphragm 8 is tightly clamped between the body halves 2 and 4 with the aid of a non-active rim portion 14, the outer periphery of which is in the shape of a beading 16, preferably but not necessarily of a substantially circular cross section and of a thickness exceeding the thickness of the non-active rim portion 14. It is of course also possible to clamp the diaphragm 8 between the body halves 2 and 4 without the beading 16, simply by having the rim portion 14 wide enough to accommodate a number of peripheral holes through which pass the bolts (not shown in FIG. 1) that hold the two halves together.

In the free, that is, non-mounted, state, the diaphragm 8 is saucer-shaped, being invertible from a first stable state in which the first of its surfaces, say surface 10, is concave and the other surface, 12, is convex, to a second stable state in which the first surface, 10, is convex and the other surface, 12, is concave. The curvature of the convex surface of the diaphragm 8 in either of the above-mentioned stable states is substantially identical with the curvatures of the concave surfaces of revolution constituting the cavity 6.

It should be added at this point that, in the mounted state, the diaphragm, when non-operative, may assume a third intermediate, stable state, in which a portion of it is attached to one wall of the cavity 6 and another portion, to the second wall. This is due to the permanent magnet constituted by the diaphragm being attracted to certain masses of ferromagnetic material which, in the non-operative state of the pump, are non-magnetic and are arranged in close proximity to the walls of the concavities forming the cavity 6.

These masses are in fact the cores and pole faces of a plurality of electromagnets in the form of substantially parallel, arcuate belts closely following the outer limits of the cavity 6. In their totality, these belts, given in FIGS. 1 and 2 even numbers on one side and odd nombers on the other side of the cavity 6, constitute an electromagnetic shell, shown to best advantage in FIG. 2. It should be noted that, for the sake of clarity, the electromagnets have been represented as belt-like, laminated solids only, none of the figures showing such obvious details as windings, terminals and leads. The belts are tightly embedded in the body halves 2 and 4, which are preferably plastic moldings, electrical connectors (not shown) being provided at the outside walls of the housing-like body. These connectors can be either of the male or of the female type, or both.

The electromagnetic belts are polarizable in the general direction of their radii of curvature. In other words, when the electromagnets are energized, the pole faces 32 become either north or south poles, depending on the direction of current flow.

While in applications dealing with nonaggressive media such as oil, inert gases and the like, the pole faces 32 can be themselves be parts of the walls forming the cavity 6 (see, e.g., FIG. 4), these walls are preferably coated with a thin layer 34 of a suitable material which, depending on the medium, may also be integral with the respective body halves.

Figure 2A:
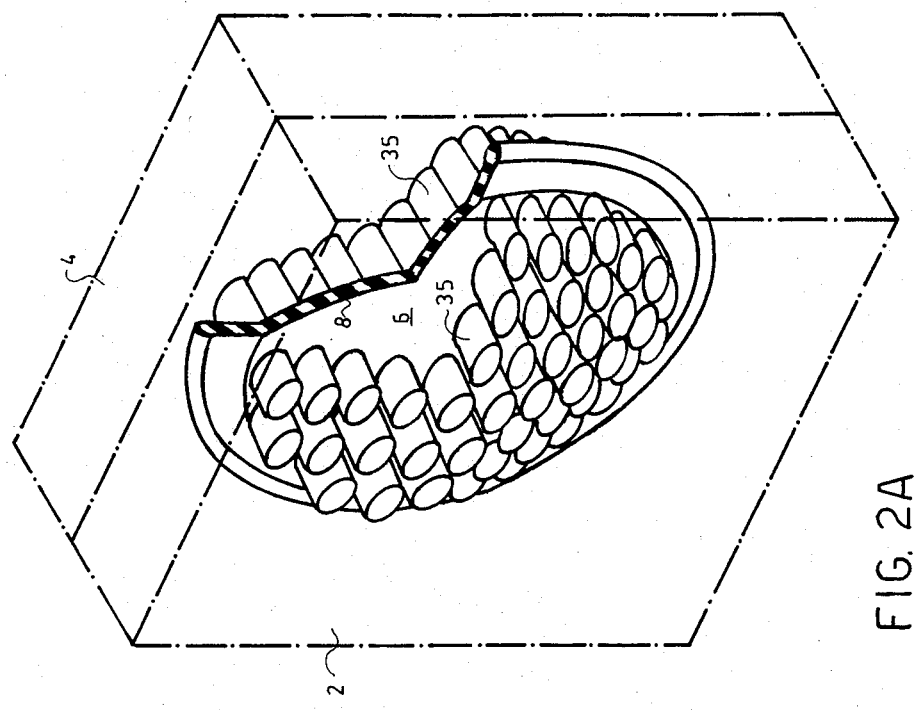
FIG. 2a is a similar view of another embodiment of the device according to the present invention.

The electromagnetic shell may also be constituted by individual electromagnets 35 disposed in a matrix-like (at least two dimensional array) arrangement closely following the outer limits of the concavity 6, as seen in FIG. 2a.

The present embodiment is furthermore provided with four ducts 36, 38, 40, 42 which end in the cavity 6, forming apertures or ports 44, 46, 48 and 50, respectively, of which, in the state shown in FIG. 1, 44 and 50 are closed by the diaphragm 8. The other ends of the ducts 36, 38, 40 and 42 lead to the outside via connecting sockets 52. The latter may also be of the female type.

The following symbols will be used in the detailed description of the operation of the universal pump according to the invention in its various embodiments:

$Ch_n$: Chamber (1,2, ... n). A chamber is the volume enclosed by one surface of the diaphragm, or a part thereof, and the opposite wall of the cavity 6. The chamber to the left of the diaphragm will be designated the subscript 1; that to the right-subscript 2. When, as in FIG. 1, one surface, 12, of the diaphragm 8 is attached to its wall over its entire area, $Ch_2=0$. The volume of the chamber enclosed by its other surface, 10, would then be $Ch_1=max$.

$Ch_n<$: In an operational sequence-the volume of chamber n increases.

$Ch_n>$: In an operational sequence-the volume of chamber n decreases.

(=) Polarization of one or several electromagnetic belts identical to the polarization of the magnetic diaphragm.

($\neq$) Polarization of one or several electromagnetic belts opposite to the polarization of the magnetic diaphragm.

(0) Electromagnetic belt or belts nor polarized.

Since identity of the polarization of two magnets can be defined as identity of the direction of the field vectors, it should be noted that, if surface 10 of the diaphragm 8 is a south pole and surface 12 is a north pole (the direction of the field vector therefore being from left to right), then, to be of identical polarization, the pole face 32 of the electromagnetic belt 29, for instance, must be a south pole. It is therefore clear that the forces acting between the diaphragm 8 and an identically polarized electromagnetic belt are forces of attraction. Conversely, forces of repulsion will act between the diaphragm and an opposite polarized electromagnetic belt.

A first, basic explanation will now be given of the operation of the device according to the invention, making reference to FIGS. 1 and 3A-3D, the latter being a schematically simplified representation of four different operational stages of the device.

Figure 3B:
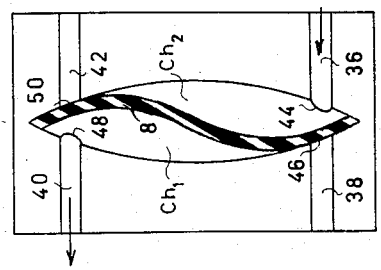
FIGS. 3A to 3D are schematic representations of the operational stages of the embodiment of FIG. 1.
Figure 3D:
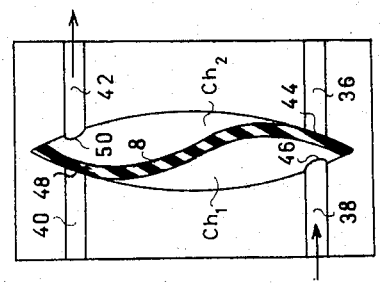
Figure 3A:
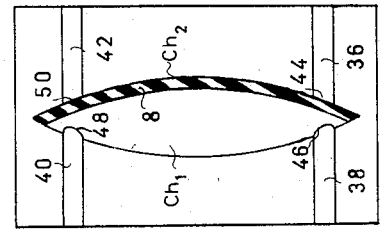

FIG. 3A is an arbitrarily chosen first stage, in which the diaphragm 8 is totally attached to the right wall and its odd-numbered electromagnetic belts 19-31. $CH_1=max$; $Ch_2=0$. The state of polarization is (=) for the odd-numbered belts and ($\neq$) for the even-numbered belts. Seen are also two inlet ports 44 and 46, of which the former is closed by the diaphragm 8, and two outlet ports 48 and 50, of which the latter is closed by the diaphragm 8.

Starting from this position, the polarization of the electromagnetic belts is progressively changed, beginning with the lowermost belt 31 which now becomes ($\neq$) and, therefore, tends to push away the diaphragm 8, and 30 which now becomes (=) and, thus, tends to attract the diaphragm 8 which rapidly flips over to the left wall, opening the inlet port 44 and closing the other inlet port 46. Chamber $Ch_2$ which, in the previous stage, was $Ch_2=0$, now becomes $Ch_2<$, thereby drawing in fluid through the inlet duct 36 and the port 44. By the same token, chamber $Ch_1$ which, in the previous stage, was $Ch_1=max$, now becomes $Ch_1>$, and fluid from the now shrinking chamber $Ch_1>$ is forced out through the outlet port 48 and the outlet duct 40. This is the beginning of a diaphragm deflection wave which, as more electromagnetic belts reverse polarity, travels upwards, further increasing $Ch_2$ and reducing $Ch_1$.

In FIG. 3B, still more electromagnetic belts have undergone polarity reversal and the deflection wave has continued to travel upwards, to a point where $Ch_2$ roughly equals $Ch_1$, more fluid having been drawn in through the port 44 and more fluid having been expelled through the port 48.

Figure 3C:
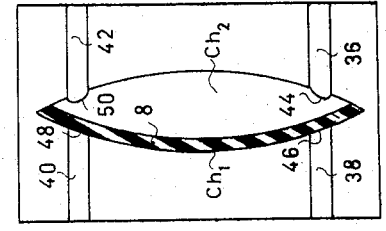

The deflection wave has completed its first half cycle in FIG. 3C, with the diaphragm 8 fully attached to the left wall, the polarization of the even-numbered belts now being (=) and that of the odd-numbered belts, ($\neq$). Both the outlet port 48 and the inlet port 46 are now closed by the diaphragm. $Ch_1=0$, all fluid having been expelled from this chamber, and $Ch_2=max$.

The stage shown in FIG. 3C, as was the stage of FIG. 3A, is an extremely short transition stage, with the polarization of the belts again progressively changing, starting with the lowermost belt 30 which now becomes ($\neq$), repelling the diaphragm zone associated with it, and belt 31 which now becomes (=), attracting the same diaphragm segment. The latter rapidly flips over to the right wall, opening the inlet port 46 and closing the other inlet port 44 (FIG. 3D). Chamber $Ch_1$ which, in the previous stage, was $Ch_1=0$, now becomes $Ch_1<$, thereby drawing fluid through the inlet duct 38 and the port 46, while chamber $Ch_2$ which, in the previous stage, was $Ch_2=max$, now becomes $Ch_2>$, and fluid from the now shrinking chamber $Ch_2$ is forced out through the outlet port 50 and the outlet duct 52. As more electromagnetic belts reverse polarity, this diaphragm deflection wave travels upwards, further increasing Ch₁ and reducing Ch₂. The uppermost belts 18 and 19 having completed their polarity reversal, the deflection wave will have concluded its second half cycle and the diaphragm 8 will have returned to the position shown in FIG. 3A.

In general terms, the output rate of the device in volume per unit time is a function of the volume of the cavity defined by one of the walls and the inside surface of the diaphragm when fully attached to the other wall, and the number of times per unit time this diaphragm flips from one wall to the other, in other words, of the frequency of the a.c. current producing the polarity reversals causing this flipping-over of the diaphragm. At a given volume of the cavity 6, a higher frequency will obviously result in a larger output rate.

The pressure attainable by the device, on the other hand, is a function of the current flowing through the windings of the electromagnetic belts. The higher the current, the larger the forces of attraction or repulsion acting between the diaphragm and the pole faces of the belts.

As to the output-vs.-time curve over a single deflection cycle of the diaphragm, it is obvious that, because of the geometry both of the cavity 6 and of the diaphragm 8, a uniform velocity of propagation of the deflection wave across the diaphragm would result in a pulsating output, as the fluid volumes associated with the individual electromagnetic belts vary with the location of those belts, being smallest with the lowermost and uppermost belts, and largest with the central belts. While for a great many applications such a pulsating output is perfectly acceptable, others may require non-pulsating outputs. Such substantially linear output curves can be achieved by suitably manipulating such operational parameters as relative operation times of different electromagnetic belts, delay times between the switching from one belt to another, as well as current intensities which affect diaphragm acceleration. Similar results can also be obtained by using a number of small-volume pumps connected in parallel and operated at high frequencies and appropriate phase shifts between separate pumps. Another method involves rigging the belts in the zone of the inlet and outlet ports in such a way as to generate a deflection wave having at least two inflection points. An arrangement like this will be discussed hereinbelow. A degree of linearity is also attainable with a single pump having a very small volume and working at high frequencies.

Returning now to FIGS. 3A–3D, an analysis of the various stages would indicate that, in stages A and C, a "short circuit", that is, a direct internal connection exists between outlet port 48 and inlet port 46, respectively outlet port 50 and inlet port 44. While, theoretically, this is indeed the case, the stages A and C, as mentioned above, are transition stages of such short duration that, for many practical applications, this will have no effect on the proper functioning of the device. In hydraulic and pneumatic systems, however, perfect internal sealing of pumps is required, both in operation and during shutdown, whether intentional or occasioned by power failure. In the device according to the invention, such complete sealing is easily achieved by the simple expedient of interconnecting the outlet duct on one side of the device, say duct 42, with the inlet duct on the other side, being duct 38. Fluid can then enter the pump only through the inlet duct 36 and is expelled from the pump only through the outlet duct 40. It would of course also be possible to interconnect the outlet duct 40 with the inlet duct 36, which would leave ducts 42 and 38 as the only active ducts. While such a procedure will obviously halve the outlet rate of the device at a given frequency (since half a diaphragm deflection cycle is now used merely to transfer the contents of one chamber into another chamber), this problem is easily solved by doubling the current frequency.

The structure and functioning of a basic embodiment of the invention, referred to in the following as universal pump, having been explained in detail, a number of embodiments based on this universal pumps will now be described.

Figure 4:
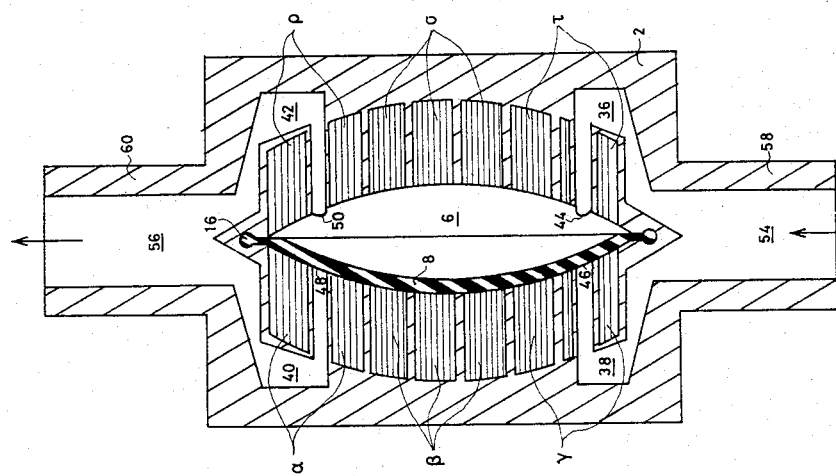
FIG. 4 is a schematic cross section of an in-line pump according to the invention.

FIG. 4 is a schematic representation of an in-line pump comprising a housing-like body 2, a cavity 6 defined and delimited by that body, a diaphragm 8 complete with beading 16, a plurality of electromagnetic belts grouped together according to the following scheme: belts 18, 20 (of FIG. 1) group $\alpha$; belts 22, 24, 26-group $\beta$; belts 28, 30-group $\gamma$; belts 19, 21-group $\rho$; belts 23, 25, 27-group $\sigma$, and belts 29, 31-group $\tau$. The groups $\alpha$ and $\rho$, $\beta$ and $\sigma$, $\gamma$ and $\tau$ are connected to three phases III, II and I, respectively of an a.c. current, with these phases having relative phase shifts of 60° (see also FIGS. 5 and 6). Further provided are inlet ports 44, 46, outlet ports 48, 50, inlet ducts 36 and 38 fed by a common inlet manifold 54, and outlet ducts 40, 42, leading into a common outlet manifold 56. The pump is connected into the fluid line with the aid of the inlet socket 58 on one side, and the outlet socket 60, on the other.

Figure 5:
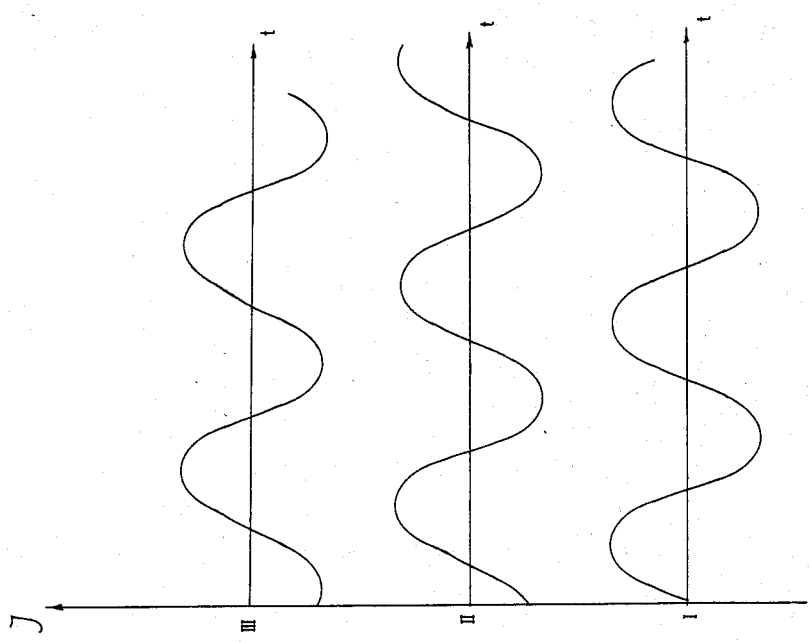
FIG. 5 represents three phases of a sinusoidal a.c. current feeding the device of FIG. 4.
Figure 6:
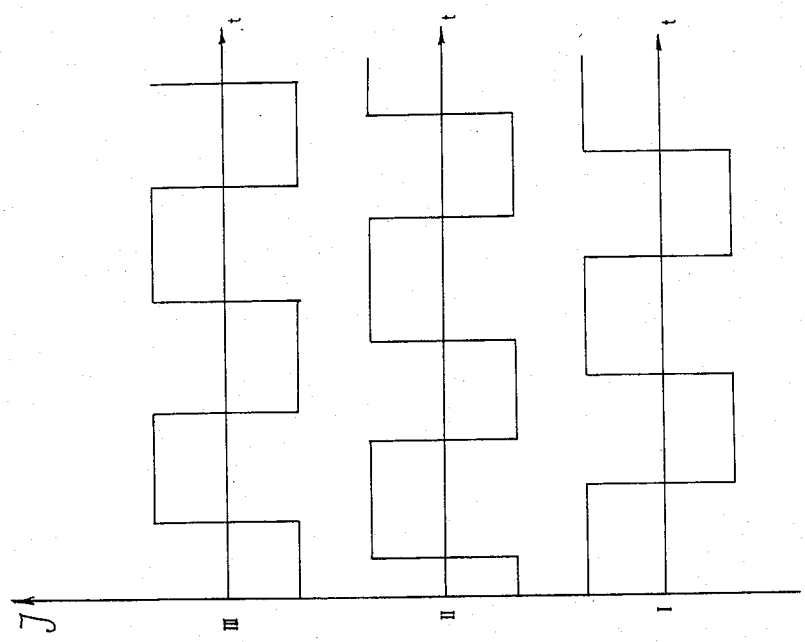
FIG. 6 represents the three phases of a square-wave a.c. current feeding the device of FIG. 4.

FIGS. 5 and 6 represent the three phases I, II, and III at their 60°-phase shift in relation to the different operational stages of the in-line pump, as shown in FIGS. 7A–7F. It is seen that the a.c. current fed to the electromagnetic belts can be sinusoidal or any other cyclic wave form, such as the square wave shown in FIG. 6. It should be noted that the phases I, II and III as drawn are associated only with the belts on one side, say, $\alpha$, $\beta$ and $\gamma$. The phases I, II and III feeding the belts $\pi$, $\sigma$ and $\tau$ would be shifted by 180° with respect to the phases shown in FIG. 5, in order to produce the opposite polarities in oppositely located pole faces. Thus, unless both are nonpolarized (0), belts $\alpha$ and $\rho$ will always be of opposite polarities, and so will belts $\beta$ and $\sigma$, as well as $\gamma$ and $\tau$.

Figure 7A:
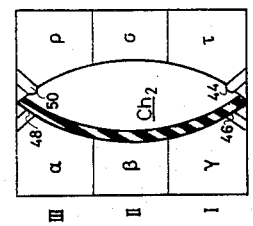
FIGS. 7A–7F are schematic representations of the different operational stages of the device of FIG. 4.

As starting point, in FIG. 7A, was arbitrarily selected the stage in which the diaphragm 8 is totally attached to the left wall of the pump. The inlet ports 44 and 46 are near the bottom of each Figure, the outlet ports 48, 50, near the top. An arrow entering a chamber $Ch_n$ through one of the inlet ports, indicates $Ch_n <$. An arrow leaving a chamber $Ch_n$ through one of the outlet ports, indicates $Ch_n >$. The states, magnetic or mechanical, of the various components of the pump are listed in Table I and, in conjunction with FIGS. 4, 5 and 7A–7F, give a clear picture of the operation of the pump.

TABLE I

Figure 7B:
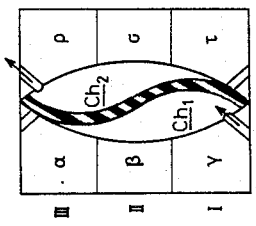
Figure 7C:
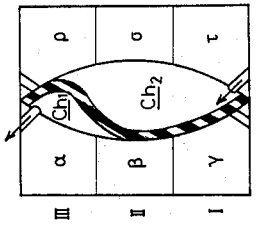
Figure 7D:
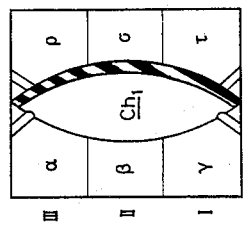
Figure 7E:
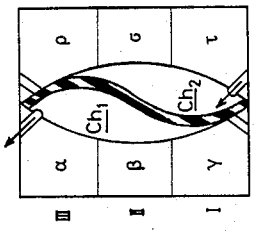
Figure 7F:
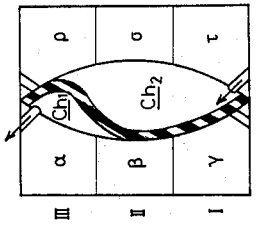

|      |         | FIG. 7A | FIG. 7B | FIG. 7C | FIG. 7D | FIG. 7E | FIG. 7F | Phase |
|------|---------|---------|---------|---------|---------|---------|---------|-------|
| Belt | $\alpha$ | =      | =       | 0       | ≠       | ≠       | 0       | III ~ |
|      | $\beta$  | =      | 0       | ≠       | ≠       | 0       | =       | II ~  |
|      | $\gamma$ | 0      | ≠       | ≠       | 0       | =       | =       | I ~   |

TABLE I-continued

|  | | FIG. 7A | FIG. 7B | FIG. 7C | FIG. 7D | FIG. 7E | FIG. 7F | Phase |
|---|---|---|---|---|---|---|---|---|
|  | ρ | ≠ | ≠ | 0 | = | = | 0 | III~ |
|  | σ | ≠ | 0 | = | = | 0 | ≠ | II~ |
|  | τ | 0 | = | = | 0 | ≠ | ≠ | I~ |
| Chamber | $Ch_1$ | zero | < | < | max | > | > | |
|  | $Ch_2$ | max | > | > | zero | < | < | |
| Inlet port | 44 | open | closed | closed | closed | open | open | |
|  | 46 | closed | open | open | open | closed | closed | |
| Outlet port | 48 | closed | closed | closed | open | open | open | |
|  | 50 | open | open | open | closed | closed | closed | |

At the completion of the stage shown in FIG. 7F, the diaphragm has completed a full cycle, having returned to the stage of FIG. 7A.

The above-described grouping and interconnections of the electromagnetic belts are of course given by way of example only. In fact, the belts themselves can be replaced by a matrix-like grid of individual electromagnets, which in some applications would make for increased efficiency.

Figure 8:
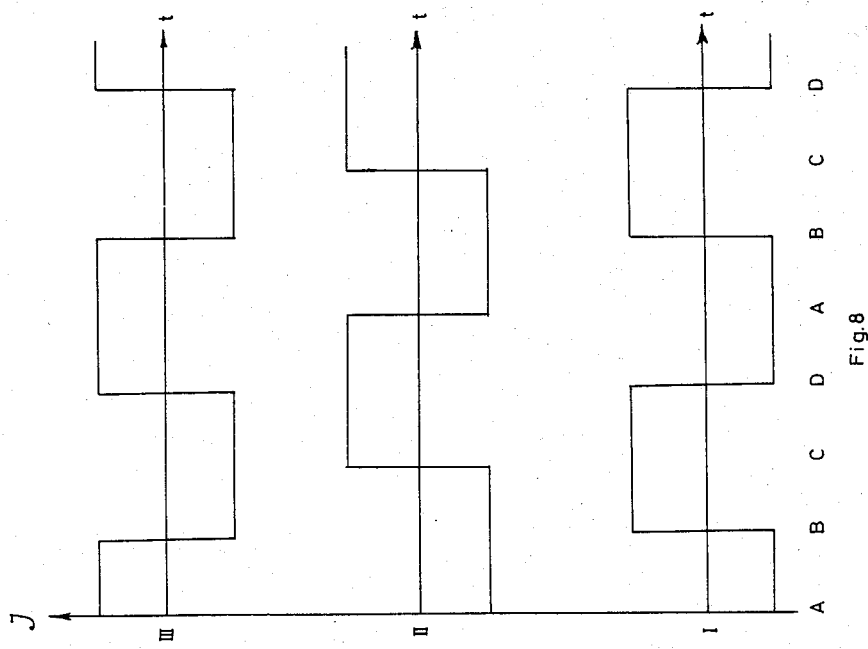
FIG. 8 represents the three phases of a square-wave a.c. current permitting digital control.

Operating the pump from an a.c. source producing three square-wave phases at a mutual shift of 90°, as shown in FIG. 8, would permit digital control of the pump in real time.

Directly derived from the individual pump as described in detail with reference to FIGS. 1 to 3A-3D are, in addition to the above discussed in-line pump, a dosing or metering pump and a perfusion or peristaltic pump, basic embodiments of which do not substantially differ, in their operational principles, from the aforementioned embodiments. A more sophisticated embodiment of the perfusion pump has a nonpulsating output, achieved either by the above mentioned method of controlling, e.g., with the aid of a microprocessor, the duration of operation of each belt or group of electromagnets, the delay times between the switching from one group to another, and the current intensities—or by controlling diaphragm deflection in such a way that, in certain stages, the cavity 6 (FIG. 1) is divided into three chambers instead of two. Such an arrangement is shown in FIGS. 9A-9D. Fed a 3-phase a.c. current at a phase shift of 90° as shown in FIG. 8, this embodiment has a uniform, nonpulsating output, achieved by the special deflection pattern of the diaphragm. As is seen in FIGS. 9B and 9D, respectively, chambers $CH_2$ and $Ch_1$ are subdivided into subchambers $Ch_{21}$, and $Ch_{22}$, respectively $Ch_{11}$ and $Ch_{12}$. It is seen that, when $Ch_{22}$ in FIG. 9B becomes progressively smaller as, naturally, does its output through outlet port 50, the total output is reinforced by the simultaneous output of $Ch_1$ through outlet port 48. A similar compensatory feature can be seen in FIG. 9D. By suitable dimensioning of all parameters concerned, a situation can be produced in which the sum of flows through the ports 48 and 50 in FIGS. 9B and 9D is a constant and also equals the flow through port 50 in FIG. 9A and through port 48 in FIG. 9C. One of these parameters is the generatrix of the surfaces of revolution constituting the cavity 6 which, in order to ensure Σflows$_{48,50}$=const., can no longer be part of a circle, but is substantially flatter in the center than near its ends. The states, magnetic or mechanical, or the various components of the pump as listed in Table II.

TABLE II

Figure 9A:
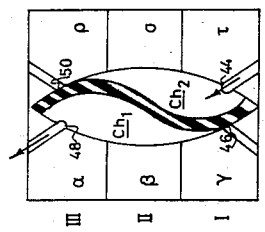
FIGS. 9A–9D are schematic representations of the operational stages of an embodiment of the invention fed an a.c. current according to FIG. 8.
Figure 9C:
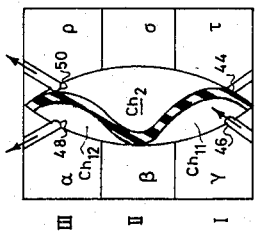
Figure 9B:
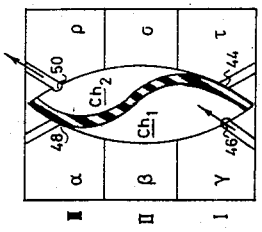
Figure 9D:
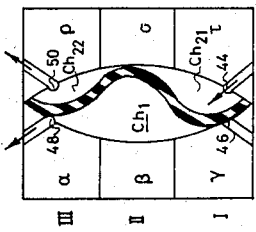
Figure 18:
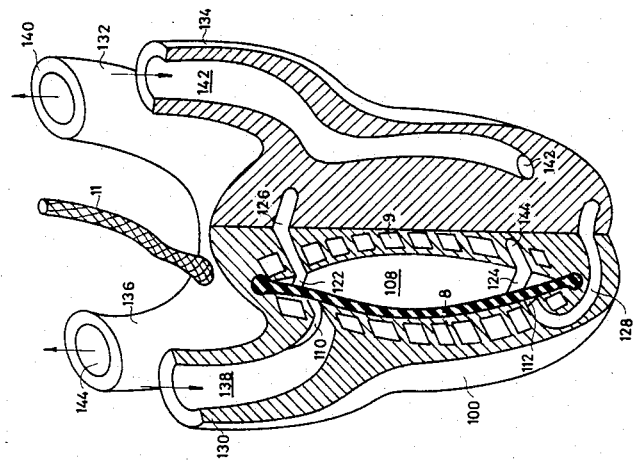
FIG. 18 is a perspective view, in partial cross section, of a synchronous artificial heart according to the invention.

|  |  | FIG. 9A | FIG. 9B | FIG. 9C | FIG. 9D | Phase |
|---|---|---|---|---|---|---|
| Belt | α | = | ≠ | ≠ | = | III~ |
|  | β | ≠ | ≠ | = | = | II~ |
|  | γ | ≠ | = | = | ≠ | I~ |
|  | ρ | ≠ | = | = | ≠ | III~ |
|  | σ | = | = | ≠ | ≠ | II~ |
|  | τ | = | ≠ | ≠ | = | I~ |
| Chamber | $Ch_1$ | < | > | > | — | |
|  | $Ch_2$ | > | — | < | > | |
|  | $Ch_{11}$ | — | — | — | < | |
|  | $Ch_{12}$ | — | — | — | > | |
|  | $Ch_{21}$ | — | < | — | — | |
|  | $Ch_{22}$ | — | > | — | — | |
| Inlet port | 44 | closed | open | open | closed | |
|  | 46 | open | closed | closed | open | |
| Outlet port | 48 | closed | open | open | open | |
|  | 50 | open | open | closed | open | |

Figure 10:
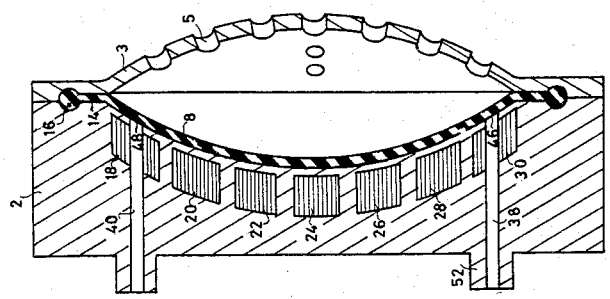
FIG. 10 is a schematic, cross-sectional view of a low-pressure, low-output embodiment of the present invention.

For low-pressure and low-output applications it is also possible to use the embodiment shown in FIG. 10 which is actually half the universal pump as shown in FIG. 1, with the optional addition of a protective cover plate 3 which serves also as clamping plate for the diaphragm 8. A number of holes 5 in the cover plate 3 serve to equalize air pressure when the diaphragm 8 is being deflected.

FIGS. 11A-11H show the various phases of the pumping cycle, starting with the empty pump. The symbols (=) and (≠) to the left of the diaphragm indicate the state of polarization of the electromagnetic belts 18 to 30 of FIG. 10. The working principle of this embodiment can be readily understood. When an opposite polarization (≠) is applied to the electromagnetic belt surrounding the inlet aperture 46 (FIG. 11A), a pocket-like "bubble" or chamber is raised, with fluid being drawn in through the inlet duct 38 and the inlet port 46. If the next higher belt is now also switched to (≠), the chamber will grow, taking in more fluid (FIG. 11B). Continued peristaltic manipulation will move the chamber upwards (FIGS. 11C and 11D). FIG. 11D concludes the "priming" stages, with the working stages proper starting in FIG. 11E, where continued polarity shifting has moved the previously produced chamber one more step upwards, while a new chamber is raised at the lowermost belt, drawing in fluid. Via a further shifting stage (FIG. 11F) the first chamber begins to discharge through outlet port 48 and outlet duct 40 in FIG. 11G and concludes discharge in FIG. 11H. The next, as well as all following working cycles conform to FIGS. 11E through 11H.

Depending upon the actual physical size of the device, it is of course possible to provide more electromagnetic belts than the seven shown by way of convenient example only and to program the polarity changes in such a way as to produce peristaltic deflection-wave trains carrying more than two fluid-filled chambers at a time.

FIGS. 12 and 12A show another embodiment of the invention, being a modular cell programmable to operate in several modes either as dosing or as peristaltic pump. The cell 2 comprises inlet ducts 36 and 38, outlet ducts 40 and 42, an electrical connector 60 of the male type, an electrical connector 62 of the female type, an on-off valve 64 for the outlet duct 40, an on-off valve 66 for the inlet duct 36, a routing valve 68 permitting internal connection or disconnection of the outlet duct 40 and the inlet duct 36, and bypass valves 70 and 72. The electrical connections are taken care of by a two-position selector switch 76. The modular cell is programmed by setting the above components. The different modes of operation are detailed below and the corresponding settings are compiled in Table III.

TABLE III

| | | Mode I | Mode II | Mode III | Mode IV | Mode V | Mode VI |
|---|---|---|---|---|---|---|---|
| Valve | 64 | closed | closed | closed | open | closed | closed |
| | 66 | open | open | open | open | closed | closed |
| | 68 | closed | closed | closed | closed | open | open |
| | 70 | closed | closed | closed | closed | closed | closed |
| | 72 | closed | closed | closed | closed | closed | closed |
| | 74 | open | open | open | closed | closed | closed |
| Selector | 76 | A | B | A | A | A | A |

Mode I: Non-pulsating output, by control of the operation times of the belts, of the delay times and of the current intensities. In the "A"-position of the selector switch 76 (see Table III), the electromagnetic belts are directly connected to the connectors 60 and 62, without any interconnections between themselves. The fluid exits through outlet duct 42. This mode permits the pump to be fed two different fluids through inlet ducts 36 and 38, respectively.

Mode II: Non-pulsating output, by producing, in some stages of the diaphragm action, a double deflection causing the pump cavity to be divided into more than two chambers (see FIGS. 9A-9D and associated description). The fluid exits through outlet duct 42. As in mode I, two different fluids may be fed to the pump through inlet ducts 36 and 38, respectively.

Mode III: Pulsating output; otherwise as mode I.

Mode IV: Pulsating output, chambers not externally interconnected as in modes I and III (via valve 74). Fluid enters through inlet ducts 36, 38 and exits through outlet ducts 40 and 42. As the two chambers are not interconnected (valves 68 and 74 being closed), two different phases entering separately through inlet ducts 36 and 38 respectively, will leave the pump, unmixed, through outlet ducts 40 and 42. Electromagnetic belts controlled by continuous successive changes of polarity.

Mode V: Pulsating output (rectangular pulses) with internal sealing (chambers connected in series). Electromagnetic belts controlled as in mode I.

Mode VI: Pulsating output with internal sealing (chambers connected in series). Electromagnetic belts controlled as in mode IV).

Shown in FIG. 12 are the actuating members of the valves 64-74 in the shape of knobs or heads which can be swiveled between an "Open" position (O) and a "Closed" position (C). Also seen is the selector switch 76 settable to an "A" or a "B" position. Both FIGS. 12 and 12A show the cell as set for mode II.

The male-female connector arrangement permits several cells to be electrically series-connected, simply by attaching them to one another.

The bypass valves 70 and 72 which, according to Table III, appear to be in the closed position in all six modes listed, serve to reduce output and/or pressure, if such reduction is needed, by shunting some of the flow back to the inlet side.

Figure 13:
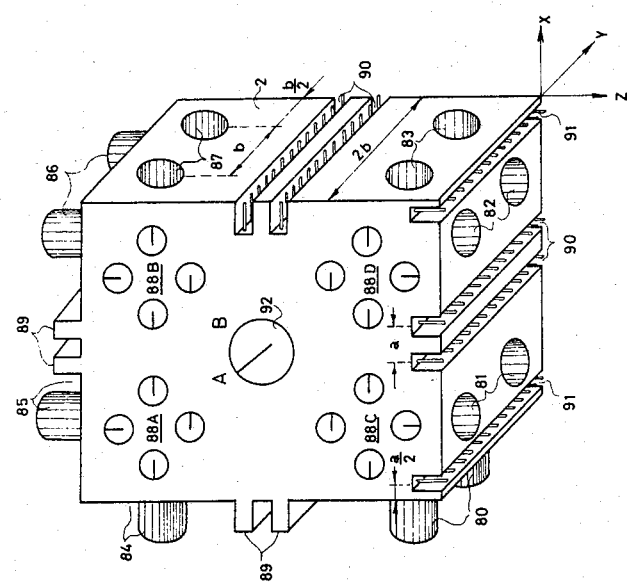
FIG. 13 is a perspective view of a universal modular cell according to the invention.

FIG. 13 is a schematic perspective view of a universal modular cell, a development of the modular cell of FIG. 12. Basically oprating on the principles underlying the universal pump of FIGS. 1 to 3, the universal modular cell is not only capable of performing the work of all previously described embodiments of the present invention but can be interconnected with any number of other cells to form "one-dimensional", "two-dimensional" and "three-dimensional" assemblies, such as schematically indicated in FIGS. 14, 15, 16 and 17, having functions to be explained below.

The universal cell of FIG. 13 is provided with a housing 2, one pair of male inlet connections 80, three pairs of female inlet connections 81, 82 and 83, three pairs of male outlet connections 84, 85 and 86 and one pair of female outlet connections 87. Internal fluid connections and routing are provided by four groups of valves 88A-D on the front face of the cell and four groups 88E-H on the (invisible) rear face. There are two male-type electrical connectors 89, each in the form of protruding twin rails and, on the respective opposite faces of the cell, two female-type electrical connectors 90. each in the form of twin grooves into which fit the twin rails of the male connectors 89 and which comprise a plurality of contact pins fitting corresponding holes in the rails. Near each of the lateral edges of the bottom face there is another, single, connector groove 91, located at a distance of a/2 from the edge, with a being the center distance of the twin connectors, both male and female. It is therefore possible to stack these universal cells not only in vertical alignment in which lower twin grooves 90 would admit upper twin rails 89, but also at a lateral offset of half the cell width, when the adjacent edge grooves 91 of two neighboring cells would together constitute a twin groove, in which would fit a twin rail 89. In addition to this offset in the x-direction, there is also a possibility of a half-cell offset in the y-direction, as the center distance between the connection apertures 87 and 83, and their male counterparts 84 and 80 is b, with the depth of the cell being 2b. While in this embodiment of the universal modular cell assembling offsets were provided for only in the x-direction (compare FIG. 16) and in the y-direction, a z-axis offset would also be possible, if edge grooves 91 were also provided on the two lateral faces of the cell. The various internal electrical connections are determined by the selector switch 92.

Figures 14, 15, 16, 17:
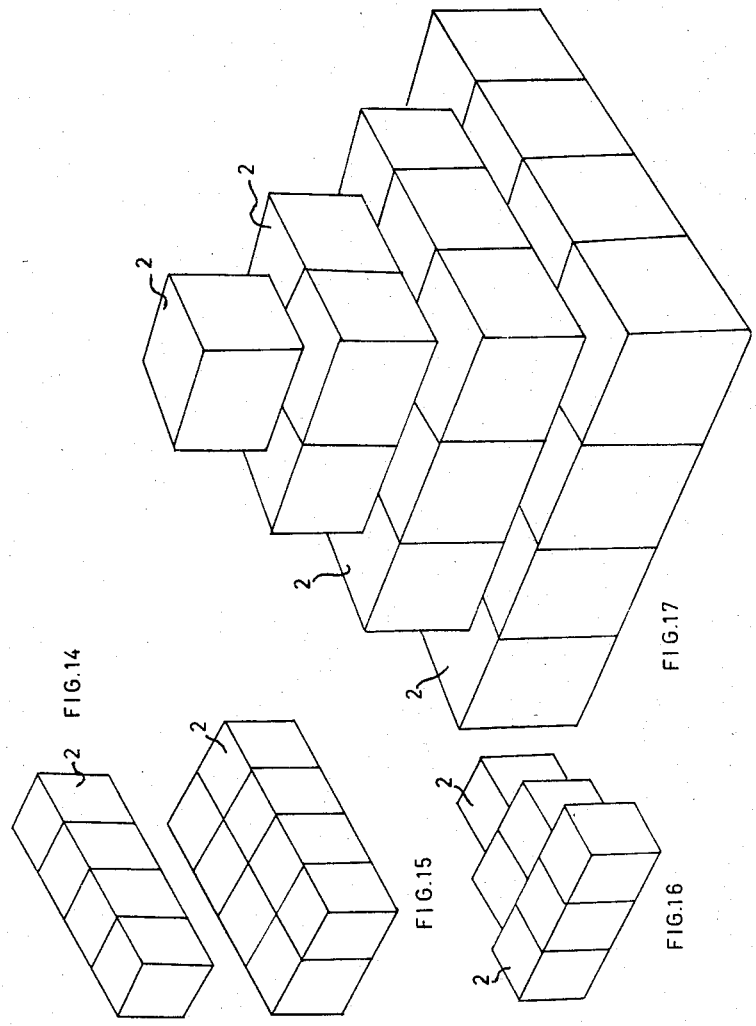
FIGS. 14 to 17 show, schematically, various possible arrangements of the universal modular cell according to FIG. 13.

FIG. 14 is a schematic perspective drawing, showing "one-dimensional" assembly of universal modular cells being connected in series and serving as a high-pressure pump for gases and liquids. As the pressure increases from stage to stage, different stages may be tapped for liquids and gases at different pressures.

FIG. 15 shows a "two-dimensional" array comprising a number of cells connected in series and in parallel. This as well as the previous embodiment may also be used to obtain liquid/gas mixtures.

FIG. 16 is another "two-dimensional" array, suitable for compressible fluids such as gases, comprising a number of cells connected in series and in parallel, with the number of cells per series-connected row gradually decreasing from a multicell low-pressure to a single-cell high-pressure stage. This embodiment is particularly designed to function either as compressor or as vacuum pump.

A "three-dimensional" array of universal cells is shown in FIG. 17. This arrangement—which may also be cubic or prismatic instead of pyramidal—is particularly useful as a complex reactor, bringing together, at different mixing ratios, pressures and, possibly, temperatures, a number of substances reacting with one another in different stages of the array, with the different reaction products available at different outlet ducts, to be withdrawn from the general process, or to be reintroduced at other stages. As due to the extreme simplicity of the underlying universal-pump design, there is, within reasonable bounds, almost no limit to the size of the cells, such as array could constitute an entire reactor plant on an industrial, rather than merely laboratory, scale, with the added advantage that such a reactor could be dismentled and reassembled in a different shape and with a different working mode for different reactions within a very short time.

A highly significant embodiment of the fluid-transfer device according to the invention is an artificial heart designed to be implanted in the human chest in place, or in support, of the natural heart. The artificial heart described in the following is of the synchronous type, i.e., the inflow of blood into the heart and the outflow of blood from the heart take place simultaneously.

Basically, the synchronous heart consists of a dual universal pump, having two diaphragms, each operating in a cavity of its own, which cavities, in a way described further below, cooperate in such a manner that, at one stage, they act as ventricula, at another stage, as auricula and, at a third stage, when divided by the deflection wave of the diaphragms, as ventricula on one side of the diaphragm and as auricula, on the other.

FIGS. 18, 19 and 20A-20D are, respectively, a perspective view in partial cross section, a cross section normal to the axis, and a diagrammatic representation of the synchronous artificial heart. There is seen the body 100 of the heart, the left auricle 102, the left ventricle 104, the right auricle 106, the right ventricle 108, the left auricle inlet valve 110, the left auricle outlet valve 112, the left ventricle inlet valve 114, the left ventricle outlet valve 116, the right auricle inlet valve 118, the right auricle outlet valve 120, the right ventricle inlet valve 122, the right ventricle outlet valve 124, the internal interconnection 126 between right auricle and right ventricle, the internal interconnection 128 between left auricle and left ventricle, the interconnection 130 to the pulmonary veins, the interconnection 132 to the aorta, the interconnection 134 to the superior and inferior venae cavae, the interconnection 136 to the pulmonary artery, the inlet 138 to the left auricle, the outlet 140 from the left ventricle, the inlet 142 to the right auricle, and the outlet 144 from the right ventricle. Also seen are the two diaphragms 8 and 8', the electromagnetic belts 9 and the electric cable 11.

As seen, FIGS. 20A-20D show different operational stages of the synchronous artificial heart. The symbols used in the following are: PV=pulmonary veins; A=aorta; PA=pulmonary artery; VC=venae cavae; LA=left auricle, RA=right auricle; LV=left ventricle; RV=right ventricle. Arterial blood is marked by dashes, venous blood by x's.

FIG. 20A represents a transitional stage in which the cavity on the left serves as the right ventricle 108, filled to maximum capacity with venous blood, and the cavity on the left serves as the left ventricle 104, filled to maximum capacity with arterial blood.

FIG. 20B is an active stage, in which the diaphragm 8 on the left, has started to deflect in direction from top to bottom. As a consequence, arterial blood from the pulmonary veins PV is drawn via LA—inlet duct 138 and LA inlet valve 110 into what now becomes the left auricle LA 102, and the venous blood in the right ventricle RV 108 is gradually forced out through the right ventricle outlet valve 124 and the RV outlet duct 144 into the pulmonary artery PA. At the same time, on the right, the diaphragm 8' has started to deflect in direction from bottom to top. As a consequence, venous blood from the venae cavae VC is dran via RA—inlet duct 142 and RA inlet valve 118 into what now becomes the right auricle RA 106, and the arterial blood in the left ventricle LV 104 is gradually forced out through the LV-outlet valve 116 and the LV outlet duct 140 into the aorta A. The stage at the completion of this active stage B is shown in FIG. 20C, a transitional stage in which the cavity on the left serves as the left auricle 102, filled to maximum capacity with arterial blood, and the cavity on the right serves as the right auricle 106, filled to maximum capacity with venous blood.

The next active stage is shown in FIG. 20D, where the diaphragm 8 has started to deflect in directon from top to bottom. As a consequence, arterial blood from the LA is being forced out via the LA-outlet valve 112 and the duct 128 connecting the LA with the LV into what is now becoming the LV 104, as the right hand diaphragm has also started to deflect, but from bottom to top, displacing, as a consequence, the venous blood from the now shrinking RA 106 and forcing it, via the RA-outlet valve 120 and the duct 126 connecting the RA 106 and the RV 108, into the now expanding RA 108. With the conclusion of this stage, the artificial heart has completed one full cycle, having returned to the initial transitional stage depicted in FIG. 20A.

FIGS. 21 and 22A-22D show another type of artificial heart based on the universal-pump principle of the present invention. This is the asynchronous heart in which, in contradistinction to the synchronous heart discussed in the foregoing, the two ventricles, left and right, do not pump blood into the body simultaneously, nor do the two auricles, left and right, draw blood from the body simultaneously. In any one of the four active stages schematically represented in FIGS. 22A and 22D only one of the ventricles and one of the auricles is active. The asynchronous heart is based on the peristaltic pump wired for double deflection of the diaphragm.

Figure 21:
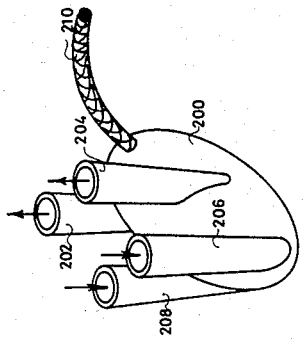
FIG. 21 is a general perspective view of an asynchronous artificial heart.

FIG. 21 is a perspective view of the asynchronous heart, showing the body 200, the tube 202, connecting the heart to the aorta (A) and leading, inside the heart, into the left ventricle (LV); the tube 204, connecting the heart to the pulmonary artery (PA) and leading into the right ventricle (RV); the tube 206, connecting the heart to the venae cavae (VC) and leading into the right auricle (RA), and the tube 208 connecting the heart to the pulmonary veins (PV), and leading into the left auricle (LA). Also seen is the electrical cable 210.

FIGS. 22A—22D show different operational stages of the asynchronous heart, the symbols used being the same as in FIGS. 20A-20D.

Figure 22:
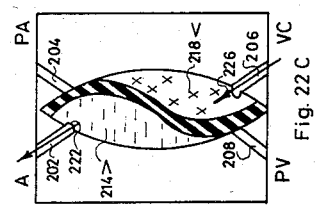
FIGS. 22A to 22D are schematic representations of different operational stages of the asynchronous heart of FIG. 21.
Figure 22:
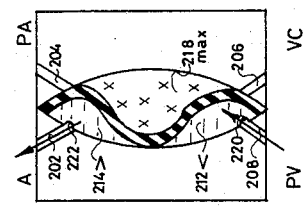
Figure 22:
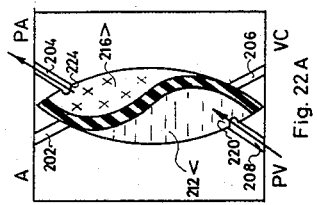
Figure 22:
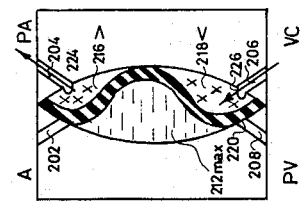

FIG. 22A shows an arbitarily selected first stage, in which deflection of the diaphragm has brought about the progressive filling of the LA 212 with arterial, oxygenated blood from the PV, through the connecting tube 208 and the valve 220, while the upward traveling deflection is reducing the volume of the RV 216, forcing the venous blood contained therein via valve 224 and connecting tube 204 into the PA. At this instant begins the double-deflection stage of the diaphragm (see FIG. 22B) which divides the cavity into three chambers: the right auricle RA 218, increasingly filled with venous blood drawn from the VC via the connecting tube 206 and the valve 226, the left auricle LA 212 filled with arterial blood and having attained its maximum size, and the right ventricle RV 216, whose decreasing size is forcing its venous blood into the PA via the valve 224 and the connecting tube 204.

In FIG. 22C the double deflection has run its course, having again turned into a single deflection which reduces the volume of the left ventricle LV 214, forcing its arterial blood via the valve 222 and the connecting tube 202 into the aorta A. At the same time, the volume of the RA 218 increases, drawing venous blood from the VC via the connecting tube 206 and the valve 226. This stage passes into the next double-deflection stage depicted in FIG. 22D, where the LA 212 expands, drawing arterialized blood from the PV via the connecting tube 208 and the valve 220, the RA 218, filled with venous blood, has attained its maximum size, and the LV 214 is being reduced, expelling its arterial blood via the valve 222 and the connecting tube 202 into the aorta A. With the completion of this stage, the heart has completed a full cycle.

Yet another artificial heart based on an embodiment of the universal pump is the compact heart, which has the form of miniature in-line pumps implanted into the major blood vessels and working at high frequency.

Figure 23A:
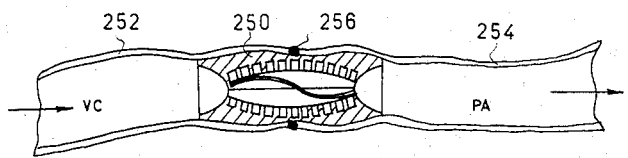
FIGS. 23A, 23B are schematic representations, in cross section, of a compact heart according to the invention, in two different operational stages.
Figure 23B:
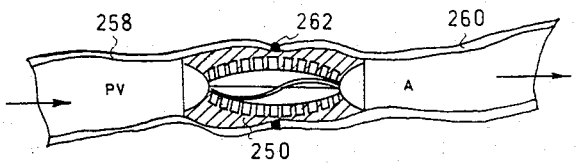

In FIG. 23A, the in-line pump 250 has been implanted partly in a vena cava 252 and partly in the pulmonary artery 254, which vessels are sutured at 256. Another in-line pump 250 has been implanted, in FIG. 23B, partly in the pulmonary vein 258 and partly in the aorta 260, which vessels are sutured at 262. The arrows indicate the directions of flow.

Figure 24A:
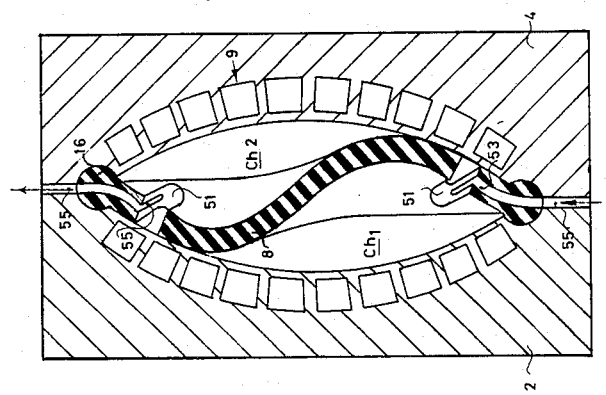
FIGS. 24A and 24B are a cross-sectional view and a partial front view, respectively, of a magnetic diaphragm with integral inlet and outlet ducts.
Figure 24B:
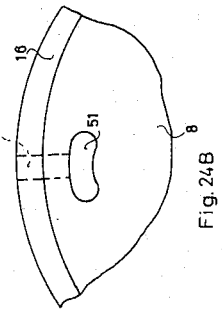

In many of the above discussed applications design of the pump could be simplified and the integrity of the electromagnetic shell improved by a diaphragm which would provide its own inlet and outlet ports and ducts. FIG. 24A is a cross-sectional view showing an in-line pump incorporating such a diaphragm. There are seen two body halves 2 and 4, the electromagnetic shells 9 and the magnetic diaphragm 8 with its beaded rim 16. Close to the rim, there are provided in diametrically opposite positions, two apertures 51, seen to better effect in FIG. 24B, passing from one surface of the diaphragm to the other. These apertures 51 can communicate with the periphery of the beading 16 via relatively narrow passage ways 53 which are in alignment with other passage ways 55 provided in the housing and leading to the outside. In the position shown in FIG. 24A, assuming the diaphragm deflection wave to travel upwards, the expanding chamber $Ch_1$ can draw fluid from the outside via the lower passage ways 55 and 53, and the lower aperture 51, while the contracting chamber $Ch_2$ can expel fluid via the upper aperture 51 and the passage ways 53 and 55, to the outside. After inversion of the diaphragm 8, chamber $Ch_1$ will be able to communicate with the outside via the upper aperture 51, while chamber $Ch_2$ will be able to do so via the lower aperture 51.

It should be noted that, in most of the applications described in this specification, the diaphragms are subjected only to flexing stresses and could therefore be designated "flexomagnetic" diaphragms. In embodiments or applications in which multiple deflections are required, the diaphragms are also subjected to a limited degree of stretching and could therefore be designated "elastomagnetic" diaphragms.

As already mentioned, the magnetic properties of the diaphragm are due to the admixture to its basic plastic or elastomeric material of a ferromagnetic substance. This substance can have the form of a ferromagnetic permanently magnetizable pulverulent particles embeddable in a matrix constituted by the above plastic or elastomeric material of the diaphragm, or in the form of prefabricated, macroscopic fragments or bodies also permanently magnetizable.

For noneritical low-output and low-pressure applications it is also possible to use diaphragms containing ferromagnetic material not permanently magnetizable. In contrast to the diaphragms described so far, diaphragms of this kind will be acted upon by forces of attraction only.

In an embodiment not shown in the figures, the roles of the housing-like body and of the diaphragm are reversed, inasmuch as the electromagnets producing the magnetic fields of controllably changing polarities and intensities are embedded in the diaphragm and interact with magnetic fields produced by permanent magnets disposed in the housing-like body of the device. Such an arrangement would be suitable primarily for very large diaphragms. The electrical leads for the electromagnets could be led out through the non-active rim of the diaphragm.

In yet another arrangement both the diaphragm and the housing-like body would be provided with electromagnets, an arrangement suitable for particularly large and powerful devices.

In still another possible arrangement the housing-like body carries a plurality of electromagnets as before, but the diaphragm is magnetically polarizable not only due to the ferromagnetic substance added to its plastic or elastomeric base, but also by means of a number of electromagnets embedded in it at strategic points, e.g., at the critical zones near the inlet and outlet ports.

It is understood that, for various particular applications, the diaphragm could include any combination of suitable magnetic-field-producing means interacting with combinations of magnetic-field-producing means disposed in the housing-like body in order to achieve the controlled dynamic deflections of the diaphragm underlying the operation of the device.

Figure 25:
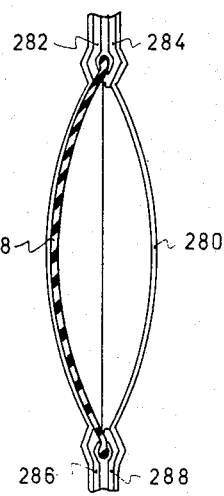
FIGS. 25 and 26 are cross-sectional views of a capsule-type cell according to the invention.

In e.g., medical and biological applications there is often a need for complete sterility which can only be ensured by pre-sterilized containers for one-time use, which are afterwards discarded. Such a discardable capsule or cartridge is shown in FIG. 25, comprising a thin-walled shell 280 with a molded-in magnetic diaphragm 8, outlet ducts 282 and 284 and inlet ducts 286 and 288. For use, the entire capsule, including equally sterilized pieces of tubing (not shown) attached to the input and output ends, is inserted into a split housing which also comprises the electromagnetic shell. With the possible aid of a sterile hypodermic needle, the inlet tubing, protruding from the housing, is connected to the vessel of the fluid to be transferred, and the outlet tubing, also provided with a needle, to the recipient of the fluid.

Figure 26:
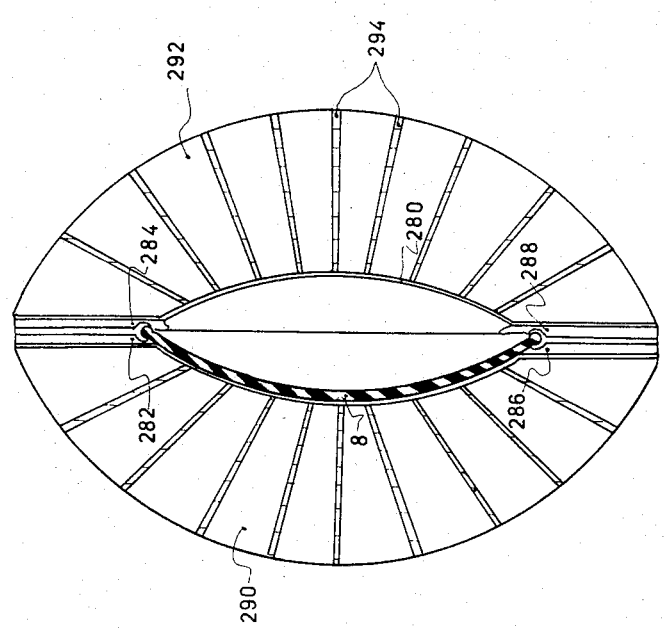

For smaller capsules, the split housing can be provided with split adaptors 290 and 292 (FIG. 26) in the form of magnetic concentrators made of shaped ferrites separated by layers of nonmagnetic material 294 which transfer the magnetic flux from the electromagnetic shells of the housing to the capsule. Such concentrators can also be provided for two or more series-connected small capsules. For substances dangerous to handle, for instance, radio-active fluids or the like, the entire process of inserting, using and discarding the capsule can be automated.

While in the embodiments so far described the force acting on the diaphragm was the result of the interaction of magnetic fields produced, on the one hand, by the elastomagnetic diaphragm and, on the other, by the plurality of electromagnets embedded in the housing, the embodiment discussed in the following is based on the electrodynamic interaction of magnetic fields produced by two electric conductors, through which d.c. currents are passed: if these currents flow in the same direction, the magnetic fields, and, consequently, the conductors producing these fields, are attracted towards each other. If the currents flow in the opposite direction, the conductors repel one another. If only one of these conductors is movable, it will in the first case move towards the other, immovable, conductors and, in the second case, away from the immovable conductor.

To utilize this well-known principle for a device according to the present invention, it is obvious that the movable conductor will be constituted by the diaphragm, while the immovable conductor will be formed by portions of the surfaces defining and delimiting the cavity 6 (FIG. 1).

Figure 27:
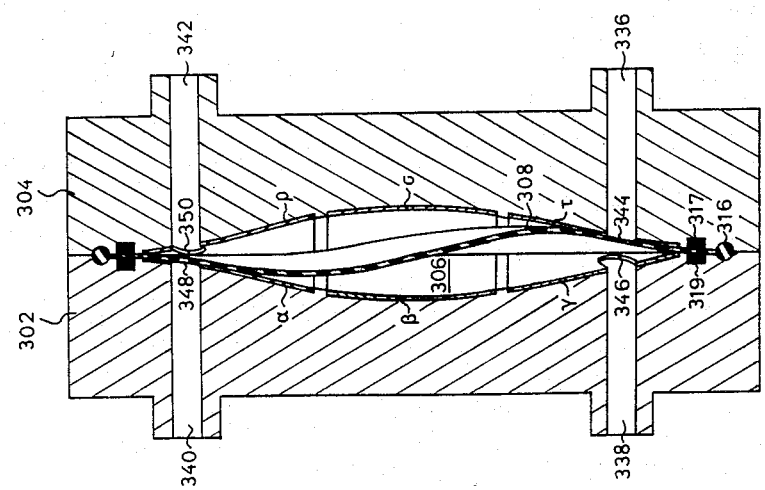
FIG. 27 is a schematic, cross-sectional view of another embodiment of the device according to the invention.
Figure 28:
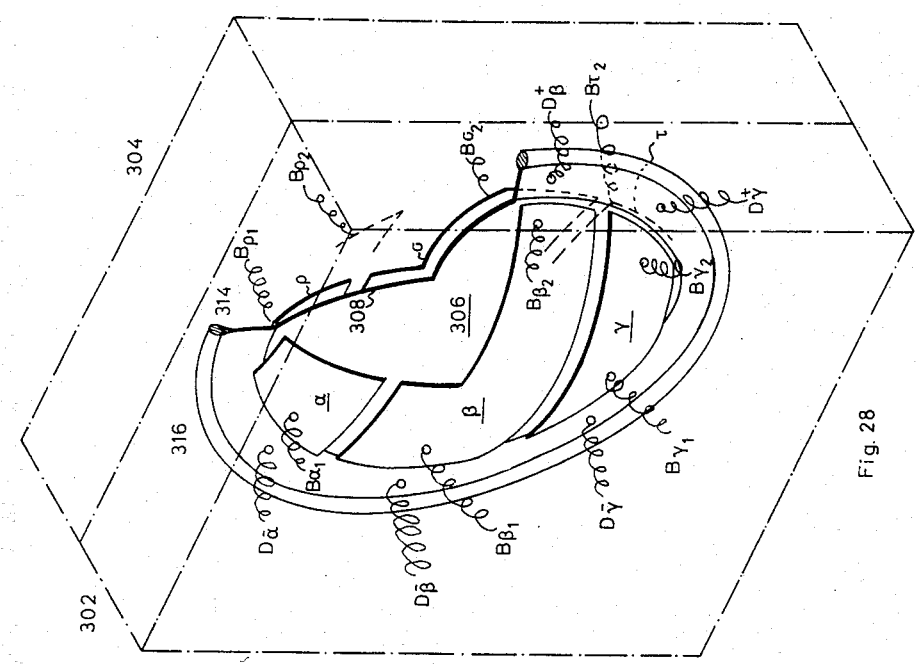
FIG. 28 is a perspective view, partly sectioned, of the interior of the embodiment of FIG. 27.

FIGS. 27 and 28 illustrate a basic embodiment of the device according to the invention, as based on the above principles.

Figure 30:
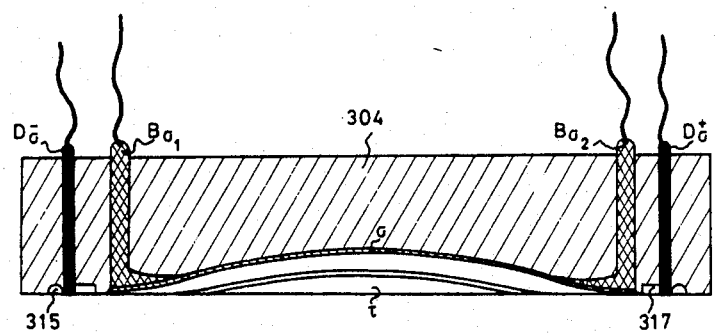
FIG. 30 is a cross-section, along plane I—I, of the housing half of FIG. 29, and FIGS. 31A–31F are schematic representations of the different operational stages of the device of FIG. 27.

In many features, this embodiment reselmbles that shown in FIGS. 1 and 2. There can be seen the body halves 302 and 304 (analogues of 2 and 4), the lenticular cavity 306 (6), the diaphragm 308 (8), the ducts 336, 338, 340 and 342 (36, 38, 40 and 42) and the parts 344, 346, 348 and 350, of which, in FIG. 27, 344 and 350 are closed. The differences are, however, important: the diaphragm 308 consists of a thin sheet of an electrically conducting material of good elastic properties, such as phosphor bronze or beryllium copper. On its periphery it is provided with a beading 316 which, in its mounted state is seated in, and retained by, corresponding grooves 315 in the housing halves 302 and 304. For definite sealing, the housing halves 302, 304 are each provided with a further groove 317, each of which accommodates an O-ring 319. The electromagnetic belts 18-31 of FIG. 1 are replaced by conductive belts of which, in this embodiment, there are provided three in each housing half: $\alpha, \beta, \gamma$ in 302, $\rho, \sigma, \tau$ in 304. These belts are constituted by very thin metal layers, in fact films, applied to the cavity surfaces by any of the known coating processes such as burning-on, chemical deposition, cathode sputtering or evaporation. Each belt is provided with an electrical connection at each of its ends. Schematically, these connections or terminals are shown in the perspective view of FIG. 28, where B stands for belt. Thus belt $\beta$ has two terminals: $B_{\beta 1}$ and $B_{\beta 2}$. The actual realization of these terminals is best seen in FIG. 30, a cross section, in the horizontal plane, through the center of body half 304. The body halves 302, 304, which are made from an electrically insulative material, such as ceramics, plastics or the like, are provided with bores which, at their cavity-side ends, are slightly flaring. Prior to the application of the metallic films constituting the belts, a good electrical conductor, e.g., silver, is poured into these bores, letting the heads of the silver "plugs" thus produced slightly project above the cavity surface. This surplus contact mass is then carefully ground away, until the "plug" is perfectly flush with the cavity surface, after which the metal films are deposited.

Figure 29:
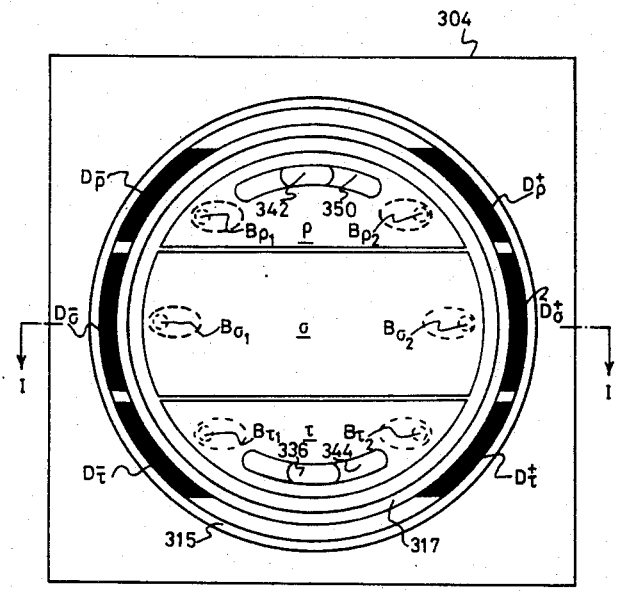
FIG. 29 is a front view of the right-hand housing half of the embodiment shown in FIG. 27.

Returning to FIG. 28, it is seen that the diaphragm 308 at its nonactive rim portion 314, is also provided with electric contacts, the letter D standing for diaphragm. It is seen, that, electrically, the diaphragm 308 is subdivided into zones roughly corresponding to the separate belts. Thus a first diaphragm zone would cover belts $\alpha$ and $\rho$, a second zone, the belts $\beta$ and $\sigma$, and a third zone, belts $\gamma$ and $\tau$. The contacts $D_\beta{}^-$ and $D_\beta{}^+$ would thus supply the $\beta$, as well as the $\sigma$ zones of the diaphragm. In critical applications, where the skin effect could make itself felt, D-contacts could also be provided on the rear side of the diaphragm rim 314, supplying the $\rho$, $\sigma$ and $\tau$ zones of the diaphragm. Thus behind $D_\beta{}^+$, there would be a contact $D_\sigma{}^+$, as shown in FIG. 30. The D-contacts are produced in the same manner as the B-contacts being clearly shown in FIG. 29, where again D-contacts are assumed to be required also on the rear side of the diaphragm 308. The signs + and −, superscripted on the letters D are meant to indicate that the direction of flow of electrical energy in the diaphragm zones is constant, the above-mentioned effect of attraction and repulsion being attained by changing the direction of flow in the belts.

Electrical energy is supplied in the form of extremely short high-energy pulses obtained by discharging capacitor banks through the belts and the diaphragms in selected sequences to obtain the earlier discussed peristaltic manipulation of the diaphragm, resulting in the pumping action. As with the rubber-type diaphragms, output is controlled by varying the peristaltic frequency. Attainable pressure is controlled by varying capacitance.

The type of electrical circuit required for such an application is well-known and used for many purposes, e.g., magnetization of permanent magnets, and need not be discussed.

In analogy to FIGS. 7A-7F, FIGS. 31A-31F shows a peristaltic pump according to the invention in six different stages. Following below is a table listing the states, electric or mechanical, of the different components of the pump, such as direction of current flow in the belts relative to direction of current flow in the matching diaphragm zones: equidirectional (=), opposite direction ($\neq$), no current flow (0); volume of chambers Ch$_1$ and Ch$_2$: zero, increasing (<), maximum, decreasing (>) and state of ports (open, closed).

TABLE IV

Figure 31A:
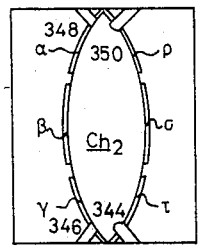
Figure 31D:
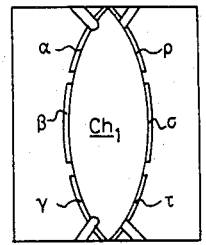
Figure 31B:
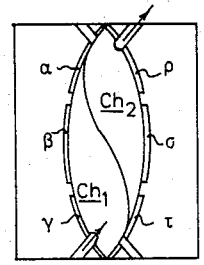
Figure 31E:
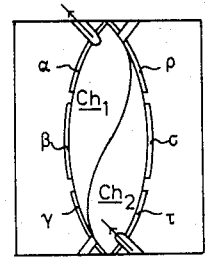
Figure 31C:
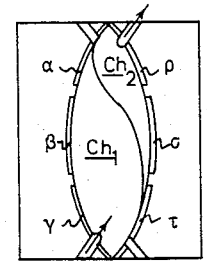
Figure 31F:
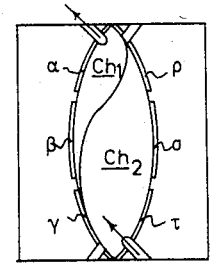

|  |  | FIG. 31A | FIG. 31B | FIG. 31C | FIG. 31D | FIG. 31E | FIG. 31F |
|---|---|---|---|---|---|---|---|
| Belt | $\alpha$ | = | $\neq$ | $\neq$ | 0 | 0 | = |
|  | $\beta$ | $\neq$ | $\neq$ | 0 | 0 | = | = |
|  | $\gamma$ | $\neq$ | $\neq$ | 0 | = | = | = |
|  | $\rho$ | 0 | 0 | = | = | $\neq$ | $\neq$ |
|  | $\sigma$ | 0 | = | = | $\neq$ | $\neq$ | 0 |
|  | $\tau$ | = | = | = | $\neq$ | $\neq$ | 0 |
| Chamber | Ch$_1$ | zero | < | < | max | > | > |
|  | Ch$_2$ | max | > | > | zero | < | < |
| Inlet port | 344 | open | closed | closed | closed | open | open |
|  | 346 | closed | open | open | open | closed | closed |
| Outlet port | 348 | closed | closed | closed | open | open | open |
|  | 350 | open | open | open | closed | closed | closed |

It has been found that, although the metallic diaphragm 308 was of one piece, the capacitor bank discharging through one of the diaphragm zones had no noticeable effect on adjacent zones, peristaltic deformation taking place as if the zones were electrically insulated from one another.

While, as stated above, the conductive diaphragm of the present embodiment is made of metal, recent developments have provided thin, nonmetallic materials of the required mechanical strength. In such a case conductive zones in the form of metallic belts would be provided on both sides of such a non-conductive carrier and could be electrically insulated from one another.

It was further found that, the electrical system supplying the diaphragm 308 being separate from that feeding the belts $\alpha, \beta, \gamma, \rho, \sigma, \tau$, there was no need to electrically insulate the diaphragm and the belts from each other, there being no danger of shortcircuiting. It is nevertheless advantageous to apply a thin, preferably elastomer, coating on either the diaphragm or the belts or on both, to reduce belt wear and noise.

It will be evident to those skilled in the art that the invention is not limited to the details of the foregoing illustrative embodiments and that the present invention may be embodied in other specific forms without departing from the essential attributes thereof, and it is therefore desired that the present embodiments be considered in all respects as illustrative and not restrictive, reference being made to the appended claims, rather than to the foregoing description, and all changes which come with the meaning and range of equivalency of the claims are therefore intended to be embraced therein.

What is claimed is:

1. A device for fluid transfer comprising:
   a housing-like body with at least one wall having at least one concavity;
   at least one elastically flexible magnetically activatable diaphragm consisting of an elastomer base to which is admixed permanent magnetic substances, said diaphragm being capable of forming, in conjunction with said concavity, one or more pocket-like chambers;
   at least one inlet aperture and at least one outlet aperture located at opposite points along the periphery of said concavity; a plurality of electromagnets arranged in proximity to said concavity and adapted to generate, in a predeterminable sequence, a plurality of magnetic fields of controllably changing polarities and intensities producing, by a combination of forces of attraction and repulsion, cycles of dynamic deflections of said diaphragm, whereby by means of said magnetically generated dynamic deflections of said diaphragm, said pocket-like chambers are peristaltically manipulated to move fluid from the region of said inlet aperture through which said fluid is drawn in, towards the region of said outlet aperture, through which said fluid is expelled.

2. The device as claimed in claim 1, wherein said housing-like body has at least two walls defining and delimiting at least one cavity, and wherein said diaphragm is capable of dividing said cavity into at least two pocket-like chambers, whereby said peristaltic manipulation of said pocket-like chambers results in the volume of at least one of said chambers being progressively increased, and the volume of at least one other of said chambers being progressively diminished.

3. The device as claimed in claim 2, wherein said cavity is of a geometry determined by the interpenetration of at least two concave surfaces of revolution facing one another with their concavities.

4. The device as claimed in claim 3, wherein said surfaces of revolution are substantially spherical.

5. The device as claimed in claim 1, wherein said diaphragm is magnetically polarized in a direction substantially perpendicular to its surfaces.

6. The device as claimed in claim 1, wherein said diaphragm in its free state, is saucer-shaped, being invertible from a first stable state in which the first of its surfaces is concave and the other surface is convex, to a second stable state in which said first surface is convex and said other surface is concave.

7. The device as claimed in claim 6, wherein the curvature of the convex surface of said diaphragm in either of said stable states is substantially identical with the curvatures of said concave surfaces of revolution of said cavity.

8. The device as claimed in claim 1, wherein said diaphragm is provided with a non-active rim portion whereby said diaphragm is mounted in said housing-like body.

9. The device as claimed in claim 8, wherein said non-active rim portion has the form of a peripheral beading.

10. The device as claimed in claim 1, wherein said electromagnets are in the form of substantially parallel, arcuate belts surrounding and closely following the outer limits of at least part of said concavity and, in their totality, constituting an electromagnetic shell.

11. The device as claimed in claim 10, wherein each of said electromagnetic belts is capable of generating with other such belts magnetic fields of controllably changing polarities and intensities.

12. The device as claimed in claim 10, wherein said belt-like electromagnets are polarizable in the general direction of their radii of curvature.

13. The device as claimed in claim 1, wherein said electromagnets are individual electromagnets disposed in a matrix-like arrangement closely following the outer limits of at least part of said concavity, said electromagnets, in their totality, constituting an electromagnetic shell.

14. The device as claimed in claim 13, wherein each of said electromagnets of said matrix-like arrangement is capable of generating magnetic fields of controllably changing polarities and intensities.

15. The device as claimed in claim 13, wherein said individual electromagnets are polarizable in the general direction towards the center of curvature of that portion of the cavity-defining wall closest to said electromagnet.

* * * * *

UNITED STATES PATENT AND TRADEMARK OFFICE
CERTIFICATE OF CORRECTION

PATENT NO. : 4,498,850
DATED : Feb. 12, 1985
INVENTOR(S) : Gena PERLOV; Samuel Tuchman It is certified that error appears in the above-identified patent and that said Letters Patent are hereby corrected as shown below:

On cover page, above Abstract, 1st line under heading

"FOREIGN PATENT DOCUMENTS" should read:

--172516 9/1968 Austria ..... 417/412--

Signed and Sealed this

Thirteenth Day of January, 1987

*Attest:*

DONALD J. QUIGG

*Attesting Officer*      *Commissioner of Patents and Trademarks*